United States Patent [19]

Stockinger et al.

[11] 4,219,650

[45] Aug. 26, 1980

[54] PROCESS FOR THE PREPARATION OF PYRROLIDONECARBOXYLIC ACID/METAL/AMINE COMPLEXES

[75] Inventors: Friedrich Stockinger, Hölstein; Friedrich Lohse, Oberwill, both of Switzerland

[73] Assignee: Ciba-Geigy Corporation, Ardsley, N.Y.

[21] Appl. No.: 956,522

[22] Filed: Oct. 31, 1978

[30] Foreign Application Priority Data

Nov. 4, 1977 [CH] Switzerland .................. 13448/77

[51] Int. Cl.$^2$ .......................... C07F 1/08; C07F 3/06; C07F 3/08; C07F 15/04
[52] U.S. Cl. .................. 546/11; 260/326.22; 528/114; 528/117; 528/407
[58] Field of Search ............ 260/326.22, 429.9, 438.1; 546/11

[56] References Cited

U.S. PATENT DOCUMENTS

| | | | |
|---|---|---|---|
| 2,819,233 | 1/1958 | Smith et al. | 260/18 |
| 2,915,540 | 12/1959 | Chang et al. | 260/429.9 |

*Primary Examiner*—Mary C. Lee
*Attorney, Agent, or Firm*—Joseph F. DiPrima; Harry Falber

[57] ABSTRACT

A process for the preparation of pyrrolidone-5-carboxylic acid/metal salt/amine complexes by reacting 1 mol of a L-glutamic acid lower alkyl ester/metal salt complex with 1 mol of an aliphatic, cycloaliphatic or aromatic-aliphatic damine or 2 mols of an aliphatic or cycloaliphatic monoamine in a polar solvent, with the elimination of 2 mols of alcohol.

The complex compounds prepared according to the invention are valuable curing agents for epoxide resins.

7 Claims, No Drawings

PROCESS FOR THE PREPARATION OF PYRROLIDONECARBOXYLIC

ACID/METAL/AMINE COMPLEXES

The present invention relates to a novel process for the preparation of pyrrolidone-5-carboxylic acid/metal-/amine complexes by reacting L-glutamic acid ester/-metal complexes with amines.

In the process for the preparation of metal/amine complexes of aliphatic carboxylic acids which has hitherto been disclosed in U.S. Pat. No. 2,819,233, the metal salts of the corresponding carboxylic acids are used as the starting materials and these are reacted with amines. When applying this procedure to the abovementioned category of compounds, it would be necessary first to prepare the metal salts of the pyrrolidone-5-carboxylic acid, which can be prepared from L-glutamic acid alkyl esters, and then to react the salts with the amines.

It is also known from U.S. Pat. No. 2,915,540 that the metal complexes of L-glutamic acid-5-(alkyl esters) can be converted to glutamine, glutamine hydrazide and glutaminehydroxamic acid by reacting the ester group with ammonia, hydrazine and hydroxylamine.

It has now been found that pyrrolidone-5-carboxylic acid/metal/amine complexes can be prepared in a simpler and thus more economical manner by reacting L-glutamic acid ester/metal complexes with amines in a polar solvent, with the elimination of the corresponding alcohol, to give the pyrrolidone-2-carboxylic acid/-metal/amine complexes.

The present invention thus relates to a process for the preparation of pyrrolidone-5-carboxylic acid/metal/a-mine complexes of the formula (Ia)

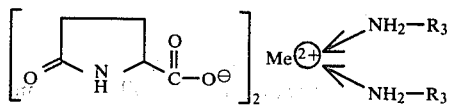

or of the formula (Ib)

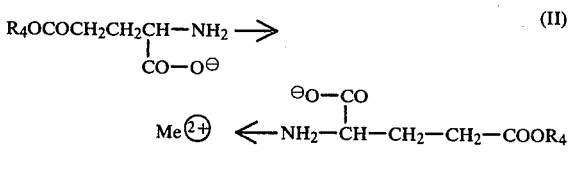

in which Me(2+) is a divalent metal cation and, if $R_1$ and $R_2$ are each a hydrogen atom, R is one of the following radicals $-CH_2(-CH_2-)_x$ in which x is a number from 1 to 6, $-CH_2-CH(OH)-CH_2-$, $-CH_2-C(CH_3)_2-CH_2-$, $(-CH_2-CH(CH_3)-O-)_y-CH_2-CH(CH_3)-$, $-CH_2-CH_2-CH_2-O(-CH_2-CH_2-O-)_y-CH_2-CH_2-CH_2-$, $-CH_2-CH_2-CH_2-O(-CH_2-CH(CH_3)-O-)_y-CH_2-CH_2-CH_2-$, or $-CH_2-CH_2-CH_2-O(-CH_2-CH_2-CH_2-CH_2-O-)_y-CH_2CH_2CH_2-$, in which y is a number from 2 to 35, $-CH(CH_3)-CH_2(-OCH(CH_3)-CH_2-)_a(-OCH_2CH_2-)_b(-OCH_2CH(CH_3)-)_c-$, in which b is a number from 10 to 50 and the sum of a and c is a number from 2 to 4,

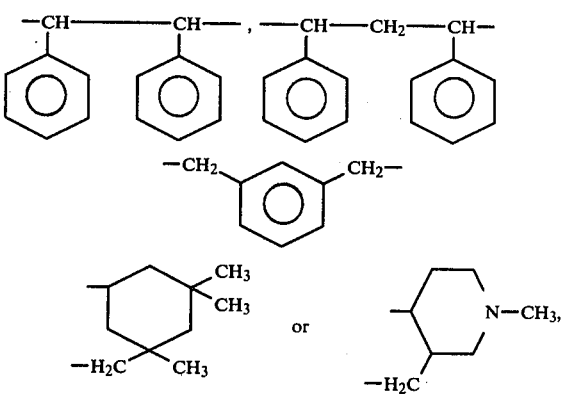

and, if $R_1$ is a hydrogen atom and $R_2$ is an alkyl having 1 to 4 C atoms, cyclohexyl, benzyl, 2-aminoethyl or 3-aminopropyl, or if $R_1$ and $R_2$ are each an alkyl having 1 to 4 C atoms, cyclohexyl or benzyl, R is an ethylene or propylene radical, and in which $R_3$ is an alkyl having 2 to 12 C atoms, 2-hydroxyethyl, 2-hydroxypropyl, benzyl, cyclohexyl or cyclopentyl, which comprises reacting 1 mol of a L-glutamic acid ester/metal complex of the formula II $$R_4OCOCH_2CH_2CH-NH_2 \rightarrow$$ (II)

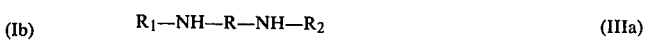

in which $R_4$ is an alkyl having 1 to 4 C atoms, cyclohexyl or benzyl with 1 mol of a diamine of the formula IIIa $$R_1-NH-R-NH-R_2 \qquad (IIIa)$$

or with 2 mols of a monoamine of the formula IIIb $$NH_2-R_3 \qquad (IIIb)$$

in a polar organic solvent and in the temperature range from 60° to 180° C., preferably 80° to 160° C., with the elimination of 2 mols of alcohol.

The compounds of the formula IIIa or IIIb which are used are preferably those in which, if $R_1$ and $R_2$ are each a hydrogen atom, R is one of the following radicals $-CH_2-(CH_2)_x-$, in which x is a number from 1 to 6, $-(CH_2-\overset{CH_3}{\underset{|}{CH}}-O)_y-CH_2-\overset{CH_3}{\underset{|}{CH}}-$, $-CH_2-CH_2-CH_2-O-(CH_2-CH_2-O)_y-CH_2-CH_2-CH_2-$, $-CH_2-CH_2-CH_2-O-(CH_2-\overset{CH_3}{\underset{|}{CH}}-O)_y-CH_2-CH_2-CH_2$, $-CH_2-CH_2-CH_2-O-(CH_2-CH_2-CH_2-CH_2-O)_y-CH_2CH_2CH_2-$, in which y is a number from 2 to 35,

[structure: -CH-CH- bridging two phenyl rings]

[structure: -CH-CH2-CH- bridging two phenyl rings with -CH2- groups attached to a third phenyl ring]

[structure: cyclohexane with CH3, CH3, CH3, -H2C, CH3 substituents] or [structure: piperidine with N-CH3 and -H2C substituent]

and, if $R_1$ is a hydrogen atom and $R_2$ is an alkyl having 1 to 4 C atoms, cyclohexyl, benzyl, 2-aminoethyl or 3-aminopropyl, or if $R_1$ and $R_2$ are each an alkyl having 1 to 4 C atoms, cyclohexyl or benzyl, R is an ethylene or propylene radical, and in which $R_3$ is an alkyl having 2 to 12 C atoms, 2-hydroxyethyl, 2-hydroxypropyl, benzyl, cyclohexyl or cyclopentyl.

The compounds of the formula II which are used are preferably the metal complexes of Zn, Co, Ni or Cd, especially those of Zn. Furthermore, the compounds of the formula II which are used are preferably the alkyl esters which contain 1 to 4 C atoms in the alkyl group.

Of the amines of the formulae IIIa and IIIb, the diamines of the formula IIIa are preferably used in the processes according to the invention. Amongst these diamines, those preferably employed are those in which, in the formula IIIa, $R_1$ and $R_2$ are each a hydrogen atom and R is one of the radicals $-CH_2-(CH_2)_x-$, in which x is a number from 1 to 6, preferably 1 to 5, $-(CH_2-\overset{CH_3}{\underset{|}{CH}}-O)_y-CH_2-\overset{CH_3}{\underset{|}{CH}}-$, $-CH_2-CH_2-CH_2-O-(CH_2-CH_2-O)_y-CH_2-CH_2-CH_2-$, $-CH_2-CH_2-CH_2-O-(CH_2-\overset{CH_3}{\underset{|}{CH}}-O)_y-CH_2-CH_2-CH_2-$, or $-CH_2-CH_2-CH_2-O-(CH_2-CH_2-CH_2-CH_2-O)_y-CH_2CH_2CH_2-$, in which y is a number from 3 to 35, or in which $R_1$ is a hydrogen atom and $R_2$ is cyclohexyl, benzyl, 2-aminoethyl or 3-aminopropyl and R is an ethylene or propylene radical.

Particularly suitable compounds of the formula IIIa are those in which $R_1$ and $R_2$ are each a hydrogen atom and R is a radical of the formula $-CH_2-(CH_2)_x$ in which x is a number from 1 to 5, or in which $R_1$ is a hydrogen atom and $R_2$ is a cyclohexyl or benzyl, 2-aminoethyl or 3-aminopropyl, and R is an ethylene or propylene radical.

Monoamines employed in the process according to the invention are preferably those compounds of the formula IIIb in which $R_3$ is an alkyl having 1 to 4 C atoms or 2-hydroxyethyl.

The L-glutamic acid ester/metal complexes of the formula II are known compounds which are obtained according to the process described in U.S. Pat. No. 2,915,540 by forming a complex from L-glutamic acid esters with the corresponding metal salts in a neutral medium.

The amines of the formulae IIIa and IIIb are also known products, most of which are available commercially.

Suitable polar organic solvents for the process according to the invention are alcohols, ethers and esters and also mixtures thereof. Examples are: glycols, especially diethylene glycol, dioxan, dibutyl ether, ethylene glycol monomethyl, monopropyl, monobutyl or dimethyl ether and the like. The more strongly polar solvents, such as dimethylformamide, dimethylacetamide and dimethylsulphoxide, are in general preferably employed in the process according to the invention. Moreover, those organic solvents which boil in the range from 80°–160° C. are preferably used.

The amount of solvent which is employed in the process according to the invention is not critical as long as the amount is sufficient to dissolve the L-glutamic acid ester/metal complex compounds therein. In general, the reaction is carried out with 20 to 60 percent by weight solutions, based on the amount of the starting material.

The complex compounds obtained by the process according to the invention are valuable curing agents for epoxide resins and the complex compounds can be employed either in catalytic amounts or in equivalent amounts.

EXAMPLE 1

Pyrrolidone-5-carboxylic acid/Zn salt/1,3-diaminopropane complex 20.68 g (0.05 mol) of L-glutamic acid-5-(ethyl ester)/Zn complex and 4.45 g (0.05 mol + 20% excess) of 1,3-diaminopropane in 50 ml of dimethylformamide are reacted for 5 hours at 124°–126° C. in a glass apparatus fitted with a stirrer, a thermometer and a reflux condenser. The pale yellow suspension is then cooled to 5° C. and filtered and the residue is washed with dimethylformamide and diethyl ether. The residue is dried at 60° C. in vacuo and this yields 16.8 g (84.9% of theory) of a white crystalline amine complex which melts at 215° to 216° C., with decomposition.

| Elementary analysis | |
|---|---|
| calculated | found |
| 39.46% C | 39.94% C |
| 5.60% H | 5.79% H |
| 14.16% N | 14.24% N |
| 16.52% Zn | 16.20% Zn |

The amine complex has the following structure:

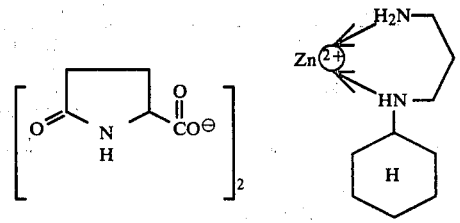

EXAMPLE 2

Pyrrolidone-5-carboxylic acid/Zn salt/N-cyclohexyl-1,3-diaminopropane complex 11.57 g (0.03 mol) of L-glutamic acid-5-(methyl ester)/Zn complex and 10.32 g (0.03 mol + 120% excess) of N-cyclohexyl-1,3-diaminopropane are reacted for 3 hours and 50 minutes in 30 g of dimethylformamide at 72°–89° C. The clear solution is then cooled to 40° C., 50 ml of acetone are added and the internal temperature is lowered to 25° C. in the course of 3 hours. The white crystalline precipitate is isolated by filtration and the residue is washed with acetone and diethyl ether and dried at 80° C. in vacuo. 9.4 g (65.4% of theory) of a white crystalline amine complex which melts at 183.4°–184.2° C. are obtained.

| Elementary analysis | |
|---|---|
| calculated | found |
| 47.38% C | 47.28% C |
| 6.70% H | 6.72% H |
| 11.63% N | 11.72% N |
| 13.57% Zn | 13.45% Zn |
| 0.80% H$_2$O | 0.80% H$_2$O |

| C$^{13}$-NMR data | |
|---|---|
| δ c | Assigned to |
| 48.7 | 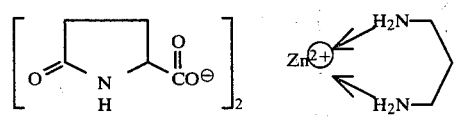 |
| 42.6 | H$_2$C—NH$_2$ |

The analytical data agree with the following complex structure:

EXAMPLE 3

Pyrrolidone-5-carboxylic acid/Zn salt/ethanolamine complex

A mixture of 9.64 g (0.025 mol) of L-glutamic acid-5-(methyl ester)/Zn complex and 3.36 g (0.05 mol + 10% excess) of ethanolamine in 30 ml of dimethylformamide is reacted for 2 hours and 45 minutes at 70° C. The clear yellowish solution is then cooled to 2° C. and stirred at this temperature for 1 hour, during which time a white crystalline precipitate separates out. The reaction mixture is filtered and the residue is washed with cooled dimethylformamide and ether and dried in vacuo at 80° C. This yields 8.2 g (73.9% of theory) of a white crystalline amine complex which melts at 120.7°–122.6° C.

| Elementary analysis | |
|---|---|
| calculated | found |
| 37.89% C | 37.90% C |
| 5.91 H | 6.05% H |
| 12.63% N | 12.48% N |
| 14.73% Zn | 14.60% Zn |

The amine complex has the following structure:

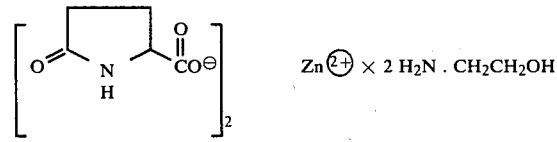

EXAMPLE 4

Pyrrolidone-5-carboxylic acid/Zn salt/N-cyclohexyl-1,3-diaminopropane complex A mixture of 20.69 g (0.05 ml) of L-glutamic acid-5-(ethyl ester)/Zn complex and 9.38 g (0.05 mol+20% excess) of N-cyclohexyl-1,3-diaminopropane in 50 ml of ethoxyethanol is reacted for 1 hour and 35 minutes at 126°–130° C., ethanol being continuously distilled off from the reaction mixture. 4.37 g of ethyl alcohol are obtained, which corresponds to a degree of conversion of 94.7% of theory.

35 ml of ether are added dropwise in the course of 10 minutes to the warm reaction mixture and the mixture is then stirred for 3 hours at room temperature and cooled at 3°–5° C. for 16 hours. The crystalline precipitate is isolated by filtration, washed with a mixture of ethoxyethanol/ether (1:2) and dried at 80° C. in vacuo. This yields 20.0 g (83.7% of theory) of a white crystalline amine complex which melts at 184°–187° C.

| Elementary analysis | |
|---|---|
| calculated | found |
| 47.48% C | 47.18% C |
| 6.79% H | 6.73% H |
| 11.66% N | 11.42% N |
| 13.60% Zn | 13.10% Zn |
| 0.58% $H_2O$ | 0.58% $H_2O$ |

EXAMPLE 5

Pyrrolidone-5-carboxylic acid/Zn salt/polyoxypropylenediamine complex 20.68 g (0.05 mol) of L-glutamic acid-5-(ethyl ester)/Zn complex and 21.28 g (0.05 mol) of polyoxypropylenediamine, which has an amine content of 4.70 amine equivalents/kg and is obtainable under the tradename "Jeffamine D-400" from the Jefferson Chemical Co., are reacted for 2 hours in 50 ml of ethoxyethanol at 125°–137° C., ethanol being distilled off continuously. 4.56 g of ethyl alcohol are split off, which corresponds to 99% of theory. The reaction mixture is then concentrated at 80° C. and under a waterpump vacuum in a rotary evaporator and dried to constant weight at 100° C./0.1 mm Hg. This yields 36.6 g (98% of theory) of a clear, brownish, highly viscous amine complex with an amine content of 2.55 amine equivalents/kg (95.3% of theory).

| Elementary analysis | |
|---|---|
| calculated | found |
| 2.40% N | 2.66% N |
| 2.74% Zn | 2.72% Zn |

The $C^{13}$-NMR data are in accord with the following complex structure:

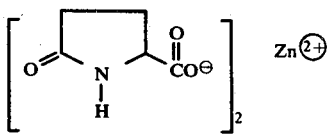

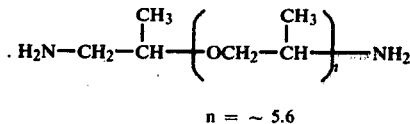

n = ~ 5.6

EXAMPLE 6

Pyrrolidone-5-carboxylic acid/Zn salt/diethylenetriamine complex

Analogously to Example 1, 23.49 g (0.05 mol) of L-glutamic acid-5-(n-butyl ester)/Zn complex, 5.67 g (0.05 mol+10% excess) of diethylenetriamine and 50 ml of dimethylacetamide are reacted for 1 hour at 130°–135° C. The reaction mixture is worked up as described in Example 1 and this yields 18.7 g (88.05% of theory) of a white crystalline amine complex which melts at 205° C.

| Elementary analysis | |
|---|---|
| calculated | found |
| 39.35% C | 39.6% C |
| 5.90% H | 6.2% H |
| 16.39% N | 16.5% N |
| 15.30% Zn | 15.25% Zn |
| 0.6% $H_2O$ | 0.6% $H_2O$ |

The amine complex has the following structure:

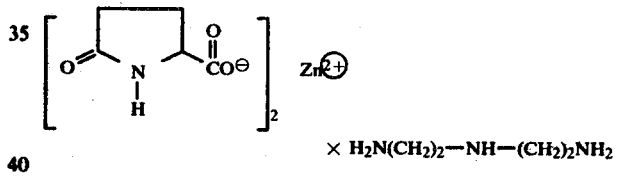

EXAMPLE 7

Pyrrolidone-5-carboxylic acid/Co salt/polyoxypropylenediamine complex

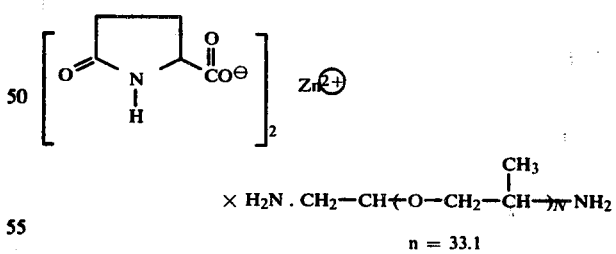

n = 33.1

In the manner described in Example 5, 75.8 g (0.2 mol) of L-glutamic acid-5-(methyl ester)/Co complex, 400 g (0.2 mol) of polyoxypropylenediamine, which has an amine content of 1.0 amine equivalent/kg, and 250 ml of dimethylacetamide are allowed to react for 1 hour and 40 minutes at 140°–162° C., during which time 12.8 g of methanol (100% of theory) are split off. The reaction mixture is worked up according to Example 5 and this yields 452 g (97.7% of theory) of a clear, viscous, dark violet amine complex with the following analytical data:

| Elementary analysis | |
| --- | --- |
| calculated | found |
| 2.41% N | 2.48% N |
| 2.53% Co | 2.35% Co |

EXAMPLE 8

Pyrrolidone-5-carboxylic acid/Zn salt/α,α'-diamino-m-xylene complex 41.4 g (0.1 mol) of L-glutamic acid-5-(ethyl ester)/Zn complex, 15.0 g (0.1 mol + 10% excess) of α,α'-diamino-m-xylene and 100 ml of dimethylformamide are reacted for 1 hour and 20 minutes at 136° C. and the ethyl alcohol which is eliminated is distilled off. The reaction mixture is cooled to 5° C. and the crystalline precipitate is filtered off and dried in vacuo at 50° C. This yields 43.6 g (95.2% of theory) of a white crystalline amine complex which decomposes at 231°–232° C. and has an amine content of 4.37 (100% of theory) amine equivalents/kg.

| Elementary analysis | |
| --- | --- |
| caluclated | found |
| 46.90% C | 47.34% C |
| 5.25% H | 5.44% H |
| 12.15% N | 12.45% N |
| 14.18% Zn | 14.0% Zn |
| 0.7% H$_2$O | 0.7% H$_2$O |

The amine complex has the following structure:

$$\left[ \begin{array}{c} \text{pyrrolidone-carboxylate} \end{array} \right]_2 \quad Zn^{2+} \leftarrow \begin{array}{c} H_2N-CH_2 \\ H_2N-CH_2 \end{array} \text{-C}_6H_4$$

What is claimed is:

1. A process for the preparation of a pyrrolidone-5-carboxylic acid/metal salt/amine complex of the formula (Ia)

$$\left[ \begin{array}{c} \text{pyrrolidone-COO}^{\ominus} \end{array} \right]_2 Me^{2+} \begin{array}{c} NH-R_1 \\ | \\ R \\ | \\ NH-R_2 \end{array} \quad (Ia)$$

or of the formula (Ib)

$$\left[ \begin{array}{c} \text{pyrrolidone-COO}^{\ominus} \end{array} \right]_2 Me^{2+} \begin{array}{c} NH_2-R_3 \\ NH_2-R_3 \end{array} \quad (Ib)$$

in which Me$^{2+}$ is a divalent metal cation and, if $R_1$ and $R_2$ are each a hydrogen atom, R is one of the following radicals $-CH_2-(CH_2)_x-$, in which x is a number from 1 to 6, $$-CH_2-CH-CH_2-,\quad -CH_2-\underset{CH_3}{\overset{CH_3}{\underset{|}{C}}}-CH_2-$$
$$\phantom{-CH_2-}\overset{|}{OH}$$

$$\left(CH_2-\underset{}{\overset{CH_3}{\underset{|}{CH}}}-O\right)_{\!y}CH_2-\underset{}{\overset{CH_3}{\underset{|}{CH}}}-,$$

$-CH_2-CH_2-CH_2-O(-CH_2-CH_2-O)_y-CH_2-CH_2-CH_2-,$ $$-CH_2-CH_2-CH_2-O\!\left(\!CH_2-\underset{CH_3}{\overset{|}{CH}}-O\!\right)_{\!y}\!CH_2-CH_2-CH_2-,$$

$-CH_2-CH_2-CH_2-O(-CH_2-CH_2-CH_2-CH_2-O)_y-CH_2CH_2CH_2-$ in which y is a number from 2 to 35.

$$-\underset{}{\overset{CH_3}{\underset{|}{CH}}}-CH_2-(OCH-CH_2)_a(OCH_2CH_2)_b(OCH_2CH)_c-$$

with CH$_3$ groups on the a and c segments in which b is a number from 10 to 50 and the sum of a and c is a number from 2 to 4, four phenyl-substituted structures (—CH—, —CH—, —CH—CH$_2$—CH—) each bearing a phenyl ring, —CH$_2$—(m-phenylene)—CH$_2$—, a dimethylcyclohexyl group (CH$_3$, CH$_3$) or —H$_2$C—(cyclohexyl with CH$_3$)

an N-methylpiperidinylmethyl group
—H$_2$C—(piperidine-N—CH$_3$)

and, if R$_1$ is a hydrogen atom and R$_2$ is an alkyl having 1 to 4 C atoms, cyclohexyl, benzyl, 2-aminoethyl or 3-aminopropyl, or if R$_1$ and R$_2$ are each an alkyl having 1 to 4 C atoms, cyclohexyl or benzyl, R is an ethylene or propylene radical, and in which R$_3$ is an alkyl having 2 to 12 C atoms, 2-hydroxyethyl, 2-hydroxypropyl, benzyl, cyclohexyl or cyclopentyl, which comprises reacting 1 mol of a L-glutamic acid ester/metal complex of the formula II $$R_4OCOCH_2CH_2\underset{\underset{CO-O^{\ominus}}{|}}{CH-NH_2} \longrightarrow \quad (II)$$

$$Me^{2+}\ \overset{\ominus O-CO}{\underset{}{\longleftarrow}} NH_2-CH-CH_2-CH_2-COOR_4$$

in which R$_4$ is an alkyl having 1 to 4 C atoms, cyclohexyl or benzyl with 1 mol of a diamine of the formula IIIa $R_1-NH-R-NH-R_2$ \hfill (IIIa)

or with 2 mols of a monoamine of the formula IIIb $NH_2-R_3$ \hfill (IIIb)

in a polar organic solvent and in the temperature range from 60° to 180° C., with the elimination of 2 mols of alcohol.

2. A process according to claim 1, wherein compounds of the formula IIIa or IIIb are used in which, if $R_1$ and $R_2$ are each a hydrogen atom, R is one of the following radicals —$CH_2$—$(CH_2)_x$—, in which x is a number from 1 to 6, —$(CH_2$—$\underset{\underset{CH_3}{|}}{CH}$—$O)_y$—$CH_2$—$\underset{\underset{CH_3}{|}}{CH}$—, —$CH_2$—$CH_2$—$CH_2$—$O$—$(CH_2$—$CH_2$—$O)_y$—$CH_2$—$CH_2$—$CH_2$—

—$CH_2$—$CH_2$—$CH_2$—$O$—$(CH_2$—$\underset{\underset{CH_3}{|}}{CH}$—$O)_y$—$CH_2$—$CH_2$—$CH_2$—

—$CH_2$—$CH_2$—$CH_2$—$O$—$(CH_2$—$CH_2$—

—$CH_2$—$CH_2$—$O)_y$—$CH_2CH_2CH_2$— in which y is a number from 2 to 35,

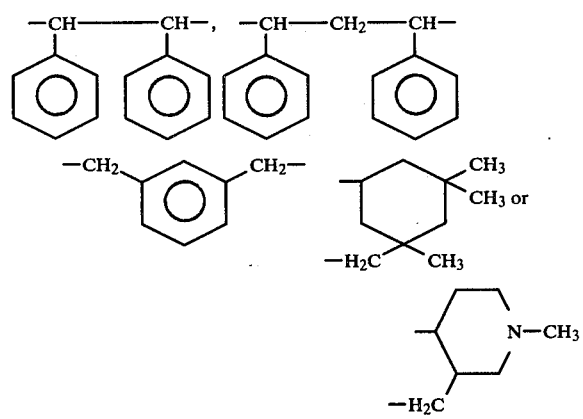

and, if $R_1$ is a hydrogen atom and $R_2$ is an alkyl having 1 to 4 C atoms, cyclohexyl, benzyl, 2-aminoethyl or 3-aminopropyl, or if $R_1$ and $R_2$ are each an alkyl having 1 to 4 C atoms, cyclohexyl or benzyl, R is an ethylene or propylene radical, and in which $R_3$ is an alkyl having 2 to 12 C atoms, 2-hydroxyethyl, 2-hydroxypropyl, benzyl, cyclohexyl or cyclopentyl.

3. A process according to claim 1, wherein compounds of the formula II are used in which Me ⊕ is a divalent metal cation of Zn, Co, Ni, Cu or Cd.

4. A process according to claim 1, wherein compounds of the formula II are used in which $R_4$ is an alkyl radical having 1 to 4 C atoms.

5. A process according to claim 1, wherein compounds of the formula IIIa are used in which $R_1$ and $R_2$ are each a hydrogen atom and R is one of the radicals —$CH_2$—$(CH_2)_x$—, in which x is a number from 1 to 5, or —$(CH_2$—$\underset{\underset{CH_3}{|}}{CH}$—$O)_y$—$CH_2$—$\underset{\underset{CH_3}{|}}{CH}$—, —$CH_2$—$CH_2$—$CH_2$—$O$—$(CH_2$—$CH_2$—$O)_y$—$CH_2$—$CH_2$—$CH_2$—

—$CH_2$—$CH_2$—$CH_2$—$O$—$(CH_2$—$\underset{\underset{CH_3}{|}}{CH}$—$O)_y$—$CH_2$—$CH_2$—$CH_2$— in which y is a number from 3 to 35, or in which $R_1$ is a hydrogen atom and $R_2$ is cyclohexyl, benzyl, 2-aminoethyl or 3-aminopropyl and R is an ethylene or propylene radical.

6. A process according to claim 1, wherein compounds of the formula IIIa are used in which $R_1$ and $R_2$ are each a hydrogen atom and R is a radical of the formula —$CH_2$—$(CH_2)_x$— in which x is a number from 1 to 5, or in which $R_1$ is a hydrogen atom and $R_2$ is a cyclohexyl or benzyl, 2-aminoethyl or 3-aminopropyl and R is an ethylene or propylene radical.

7. A process according to claim 1, wherein a compound of the formula IIIb is used in which $R_3$ is an alkyl having 1 to 4 C atoms or 2-hydroxyethyl.

* * * * *